(12) United States Patent
Kiss

(10) Patent No.: US 11,029,436 B2
(45) Date of Patent: Jun. 8, 2021

(54) SYSTEM AND METHOD FOR MEASURING SOIL ELECTRICAL CONDUCTIVITY

(71) Applicant: Tribus, LLC, Dodge City, KS (US)

(72) Inventor: Michael Z. Kiss, Costa Mesa, CA (US)

(73) Assignee: TRIBUS, LLC, Dodge City, KS (US)

( * ) Notice: Subject to any disclaimer, the term of this patent is extended or adjusted under 35 U.S.C. 154(b) by 0 days.

(21) Appl. No.: 16/172,720

(22) Filed: Oct. 26, 2018

(65) Prior Publication Data

US 2019/0324168 A1 Oct. 24, 2019

Related U.S. Application Data

(60) Provisional application No. 62/577,637, filed on Oct. 26, 2017.

(51) Int. Cl.
*G01V 3/02* (2006.01)
*G01N 33/24* (2006.01)
*G01K 13/00* (2021.01)

(52) U.S. Cl.
CPC .............. *G01V 3/02* (2013.01); *G01K 13/00* (2013.01); *G01N 33/246* (2013.01)

(58) Field of Classification Search
CPC ... G01N 33/24–246; G01K 13/00; G01V 3/02
See application file for complete search history.

(56) References Cited

U.S. PATENT DOCUMENTS

| | | | |
|---|---|---|---|
| 5,418,466 A | 5/1995 | Watson et al. | |
| 7,408,364 B1 * | 8/2008 | Campbell | G01N 33/246 324/644 |
| 8,285,503 B1 * | 10/2012 | Anderson | G01R 27/04 702/79 |
| 8,981,946 B2 * | 3/2015 | Runge | A01G 25/167 137/78.2 |
| 9,797,814 B2 * | 10/2017 | Mottes | G01N 33/24 |
| 2002/0167412 A1 * | 11/2002 | Cuming | G01N 27/048 340/602 |
| 2004/0145379 A1 | 7/2004 | Buss | |
| 2010/0194411 A1 | 8/2010 | Caron | |
| 2010/0301877 A1 * | 12/2010 | Paterson | G01N 33/246 324/664 |

(Continued)

FOREIGN PATENT DOCUMENTS

WO 2017/021950 A2 2/2017

OTHER PUBLICATIONS

Sentek Pty Ltd, TriSCAN Agronomic User Manual, Version 1.2a, 2003, Stepney, South Australia.

*Primary Examiner* — Huy Q Phan
*Assistant Examiner* — David B Frederiksen
(74) *Attorney, Agent, or Firm* — Jack D. Stone, Jr.; Scheef & Stone, L.L.P.

(57) ABSTRACT

A probe relies on multiple sensors, which are capable of directly measuring soil moisture, temperature, and electrical conductivity (EC). The proposed probe uses radio frequency ("RF") transformers to sense changes in load by the primary of the transformer, which will make direct contact with the soil. The probe contemplated herein, accurately measures EC values in liquids, and water saturated soils, by having direct contact with the medium in which the measurements are made. The measurements yield absolute EC, in any soil type.

7 Claims, 7 Drawing Sheets

(56) References Cited

U.S. PATENT DOCUMENTS

| | | | |
|---|---|---|---|
| 2015/0180486 A1* | 6/2015 | Shanan | H03L 7/099 327/156 |
| 2015/0323491 A1* | 11/2015 | Miller | G01N 27/4035 205/789 |
| 2016/0183484 A1* | 6/2016 | Richings, Sr. | A01G 25/167 239/11 |
| 2016/0223511 A1 | 8/2016 | Koshnick et al. | |
| 2017/0067869 A1* | 3/2017 | Lund | G01N 33/246 |
| 2017/0332566 A1* | 11/2017 | Emory | F16K 31/001 |
| 2018/0224382 A1* | 8/2018 | Golombek | G01N 33/246 |
| 2018/0328513 A1* | 11/2018 | Emory | A01G 25/167 |

\* cited by examiner

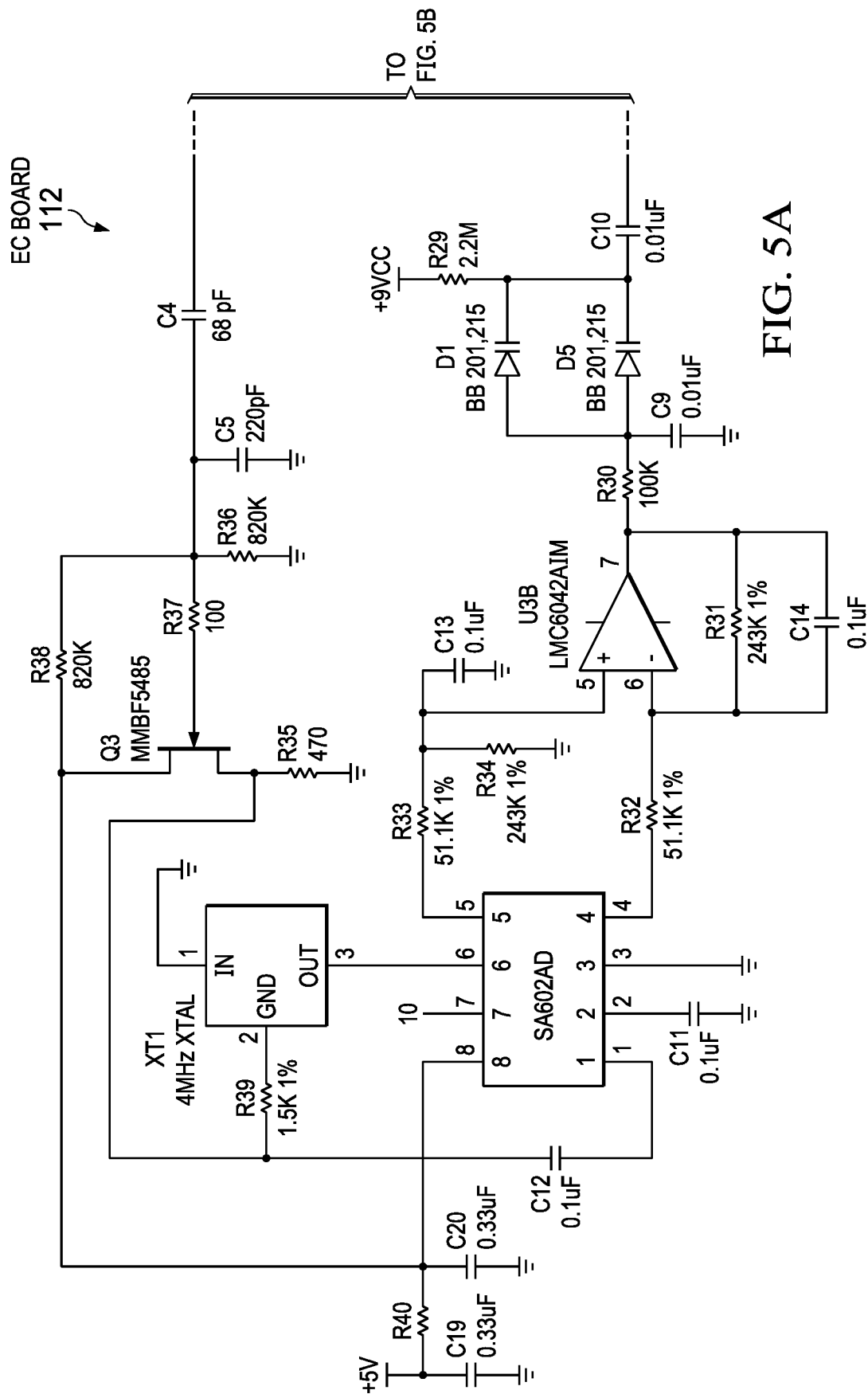

SYSTEM AND METHOD FOR MEASURING SOIL ELECTRICAL CONDUCTIVITY

CROSS-REFERENCE TO RELATED APPLICATIONS

This application claims the benefit of U.S. Provisional Application No. 62/577,637, filed Oct. 26, 2017, which applications is hereby incorporated herein by reference, in its entirety.

TECHNICAL FIELD

The invention relates generally to directly measuring soil electrical conductivity.

BACKGROUND

Soil electrical conductivity ("EC") is a measure of the amount of salts in soil (salinity of soil). It is an important indicator of soil health. It affects crop yields, crop suitability, plant nutrient availability, and activity of soil microorganisms which influence key soil processes including the emission of greenhouse gases such as nitrogen oxides, methane, and carbon dioxide. Excess salts hinder plant growth by affecting the soil-water balance. Soils containing excess salts occur naturally in arid and semiarid climates. Salt levels can increase as a result of cropping, irrigation, and land management. EC has been correlated to concentrations of nitrates, potassium, sodium, chloride, sulfate, and ammonia. For certain non-saline soils, determining EC can be a convenient and economical way to estimate the amount of nitrogen (N) available for plant growth. When irrigating, additional water beyond crop needs can be used to flush excessive salts below the root zone and maintain an EC level, which is based on crop tolerance.

In view of the foregoing, EC data will track nitrates in the crop rooting zone allowing for better nitrogen management, reducing nitrogen leaching past the crop root zone and reduce ground water contamination. Monitoring soil moisture and EC will also help determine irrigation application rates throughout the growing season.

Unfortunately, the probes which are available in today's market make use of capacitive sensors, which do not make direct contact with the soil. See, for example, TriSCAN Agronomic User Manual Version 1.2a of Sentek Pty Ltd, Stepney, South Australia, showing EC measurements using capacitive probes. There, capacitance based soil profile probes are installed vertically into the soil, and do not make direct contact with the soil. The capacitive sensors are isolated from the soil, and installed inside plastic "access tubes", at each depth of interest. The EC values are derived from measurements of "volumetric ion content" which are used to calculate the EC value for each specific soil type.

This method of EC measurement is flawed, as soil types are not homogeneous. The data model uses a nominal volumetric ion content (VIC), and the units of the VIC can only be related to the soil EC, through site quantitatively specific soil sampling and analysis.

In view of the foregoing, there is a need for a system and method for measuring soil electrical conductivity more effectively.

SUMMARY

The present invention, accordingly, provides a probe which relies on multiple sensors, which are capable of measuring soil moisture, temperature, and electrical conductivity (EC). The probe of the invention will use radio frequency ("RF") transformers to sense changes in load by the primary of the transformer, which will make direct contact with the soil.

The probe contemplated here accurately measures EC values in liquids and water saturated soils by having direct contact with the medium in which the measurements are made. The measurements yield absolute EC in any soil type.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIGS. 5A-5C are schematic drawings of a circuit embodying features of the present invention.

DETAILED DESCRIPTION

Figure 1:
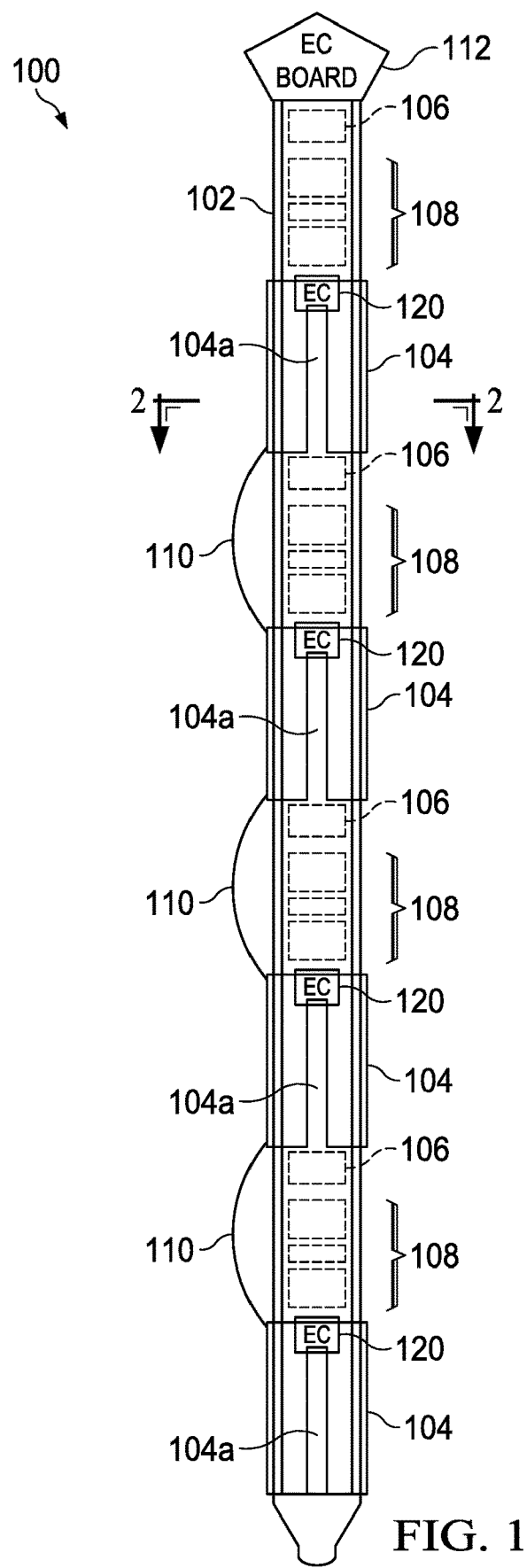
FIG. 1 exemplifies a probe configured for measuring moisture, temperature, and electrical conductivity of soil in accordance with one embodiment of the invention.

Refer now to the drawings wherein depicted elements are, for the sake of clarity, not necessarily shown to scale and wherein like or similar elements are designated by the same reference numeral through the several views. In the interest of conciseness, well-known elements may be illustrated in schematic or block diagram form in order not to obscure the present invention in unnecessary detail, and details concerning various other components known to the art, such as microprocessors, temperature sensors, moisture sensors, and the like necessary for the operation of many electrical devices, have not been shown or discussed in detail inasmuch as such details are not considered necessary to obtain a complete understanding of the present invention, and are considered to be within the skills of persons of ordinary skill in the relevant art. Additionally, as used herein, the term "substantially" is to be construed as a term of approximation.

It is noted that, unless indicated otherwise, many functions described herein may be performed by a processor such as a microprocessor, a controller, a microcontroller, an application-specific integrated circuit (ASIC), an electronic data processor, a computer, or the like, in accordance with code, such as program code, software, integrated circuits, and/or the like that are coded to perform such functions.

Furthermore, it is considered that the design, development, and implementation details of all such code would be apparent to a person having ordinary skill in the art based upon a review of the present description of the invention.

Referring to FIG. 1 of the drawings, the reference numeral 100 generally designates a probe embodying features of the present invention for measuring soil moisture, temperature, and electrical conductivity ("EC"). The system 100 includes a tube 102, preferably about an inch in outer diameter and fabricated from a non-metallic material or plastic, such as PVC (polyvinyl chloride), in a manner well-known in the art.

In one preferred embodiment, tube 102 includes four stainless steel sleeves 104 about one to two inches long with a slot 104a defined on each of two opposite sides of the sleeve. Slot 104a extends longitudinally substantially along the length of the sleeve, but short of the entire length. While four sleeves 104 are exemplified in FIG. 1, more or less sleeves may be utilized as suitably appropriate. Sleeves 104 are preferably electrically coupled via a wire 110 for effecting a ground. As discussed in further detail below, sleeves 104 acts as a primary of an EC sensor radio frequency ("RF") transformer.

A conventional temperature sensor 106 and moisture sensor 108 are interposed between and above each sleeve 104, and between the tube outer wall 102 and an inner wall 114 (FIG. 2) of probe 100. Moisture sensor 108 is preferably of the type to utilize two relatively wide copper bands with a more narrow copper band between the wider copper bands. Such temperature sensors and moisture sensors are considered to be well known in the art and, therefore, will not be described in further detail herein, except insofar as necessary to describe the invention.

Figure 2:
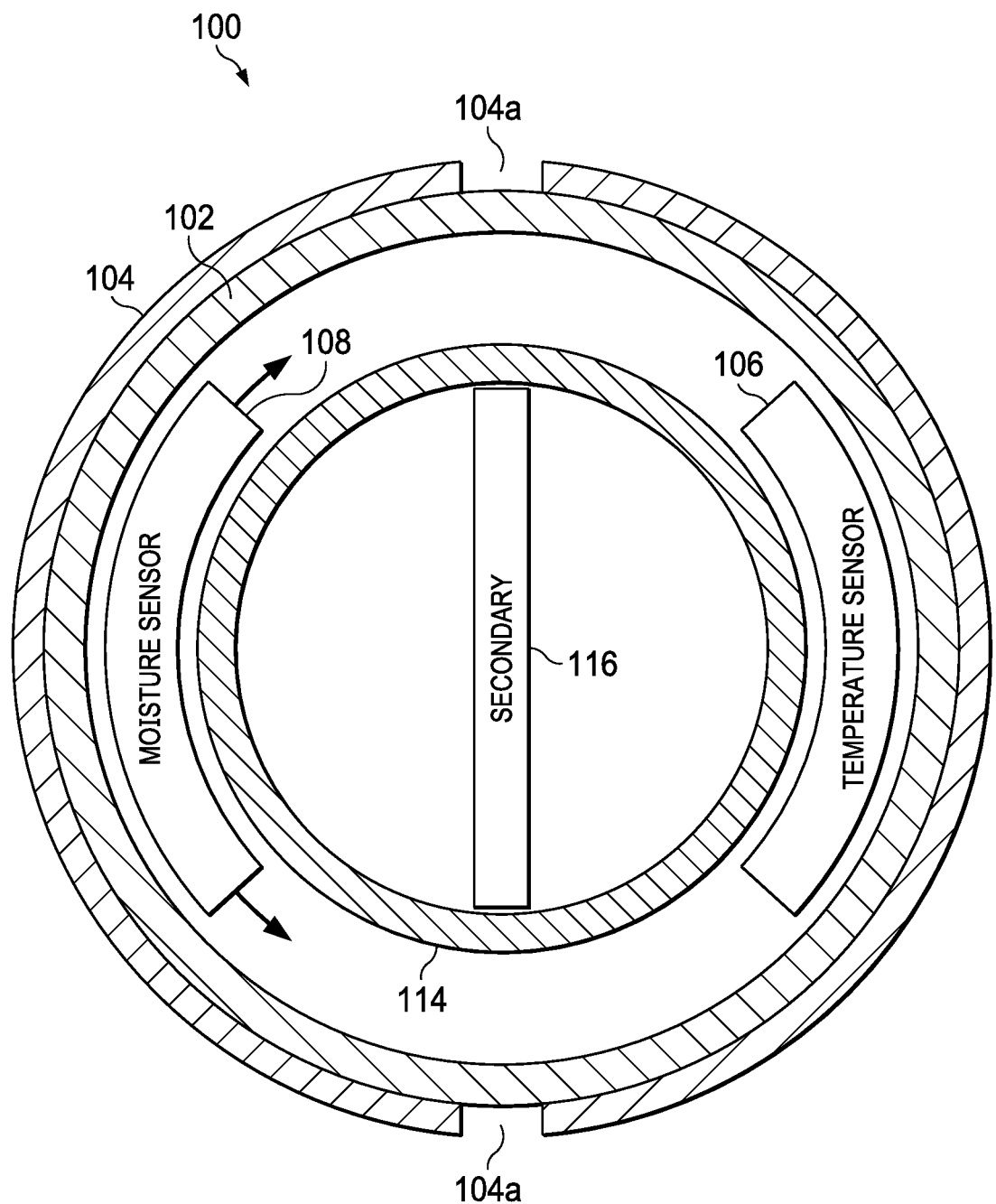
FIG. 2 is a cross-section of the probe of FIG. 1 taken along the line 2-2 of FIG. 1.
Figure 3:
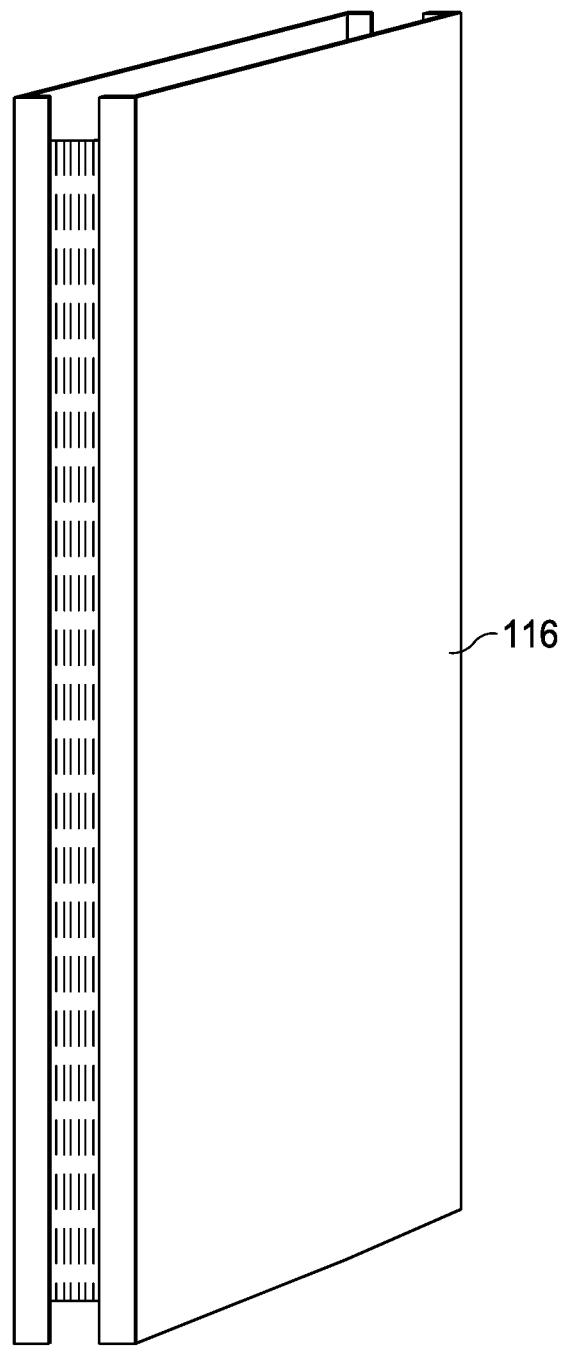
FIG. 3 exemplifies an electrical conductivity sensor bobbin for use with the probe of FIG. 1.

FIG. 2 depicts a cross-section of the probe of FIG. 1 taken along the line 2-2 of FIG. 1. As shown therein, probe 100 includes an inner tube or wall 114. As shown, an EC sensor RF transformer secondary 116 wound on an acetal or similar substantially temperature-stable, non-electrically-conductive bobbin (FIG. 3) is positioned within the inner wall in alignment with slots 104a. A distinct secondary 116 is provided corresponding to each primary 104, and the length of each secondary 116 approximates the length of slot 104a. The EC sensor RF transformer primary 104 and EC sensor RF transformer secondary 116 are collectively referred to herein as EC sensor 120. As mentioned above and shown more clearly in FIG. 2, multiple temperature sensors 106 and moisture sensors 108 are interposed between the tube outer wall 102 and an inner wall 114 of probe 100.

Figure 4:
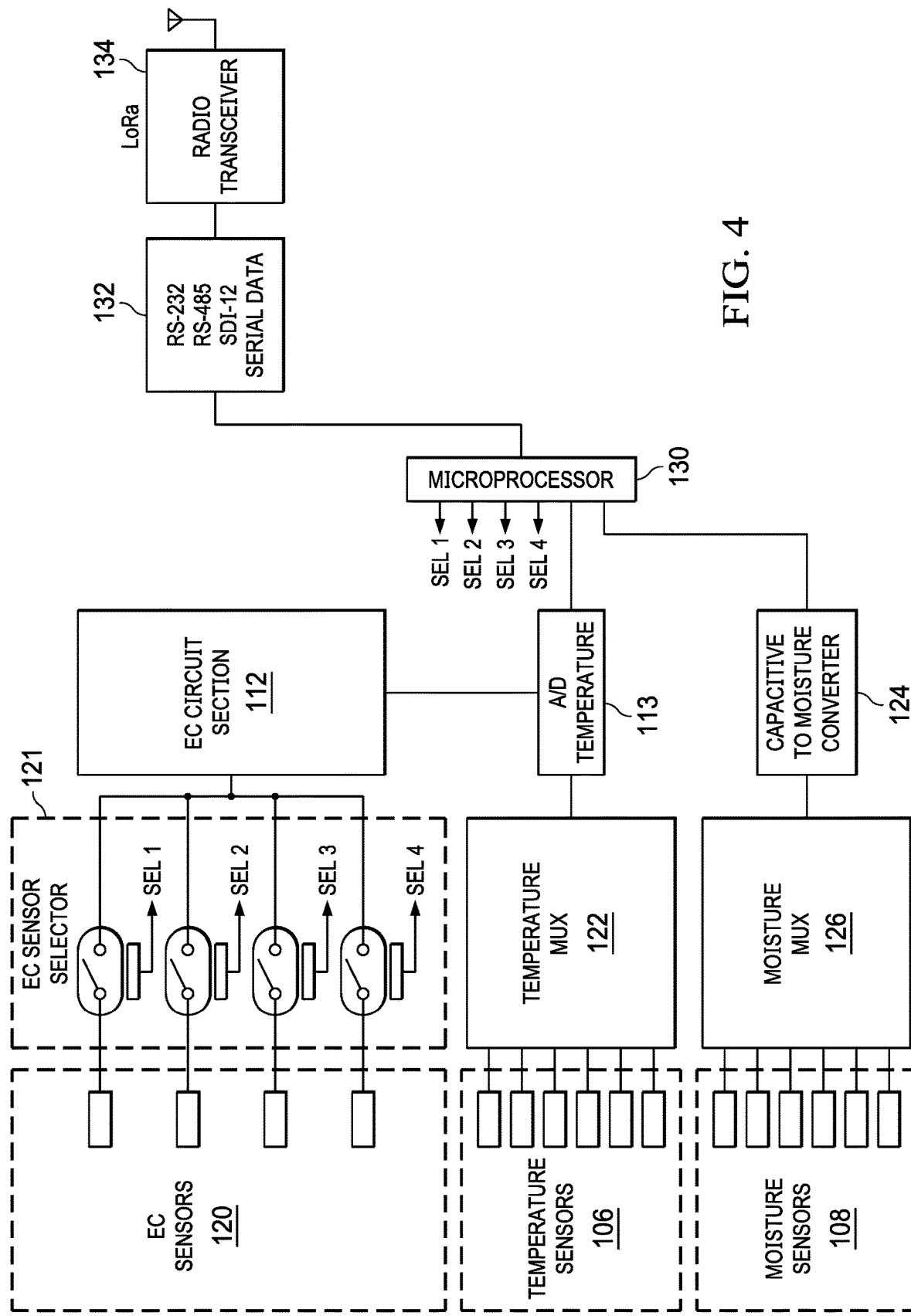
FIG. 4 is a block diagram exemplifying one system embodying features of the present invention.

FIG. 4 is a block diagram of a system for monitoring soil temperature, moisture, and electrical conductivity. As shown, EC sensors 120 are coupled to an EC circuit board 112 discussed in further detail below with respect to FIGS. 5A-5C. EC board 112 generates an output to an analog-to-digital ("A/D") converter 113, which then converts the analog signal to a digital signal which is transmitted to a microprocessor 130. Still further, as indicated by an arrow on each EC sensor selector 121 (e.g., a reed switch, MOSFET, or the like) and a corresponding arrow on microprocessor 130, each EC sensor 120 generates a signal directly to A/D converter 113, which converts the analog signal to a digital signal which is transmitted directly to microprocessor 130.

Multiple temperature sensors 106 generate multiple signals preferably to a multiplexer 122, which then transmits a single signal to an analog-to-digital converter 113, which converts actual capacitance to a digital signal compatible with, and transmitted to, microprocessor 130. Multiple moisture sensors 108 generate multiple signals preferably to a multiplexer 126, which then transmits a single signal to converter 124, which in turn generates a signal to microprocessor 130.

Microprocessor 130 receives signals from EC sensors 120, from the EC board 112, from the temperature sensors 106, and from the moisture sensors 108, and from those signals generates a serial data signal 132 comprising electrical conductivity, temperature, and moisture information. By way of example, the serial data signal 132 conforms to RS-232, RS-485, and/or SDI-12, and is transmitted, preferably via a radio transceiver 134, to a central monitoring facility (not shown).

In a preferred embodiment, all components of FIG. 4, except the radio transceiver 134, are housed within probe 100, preferably proximate EC board 112.

Figure 5B:
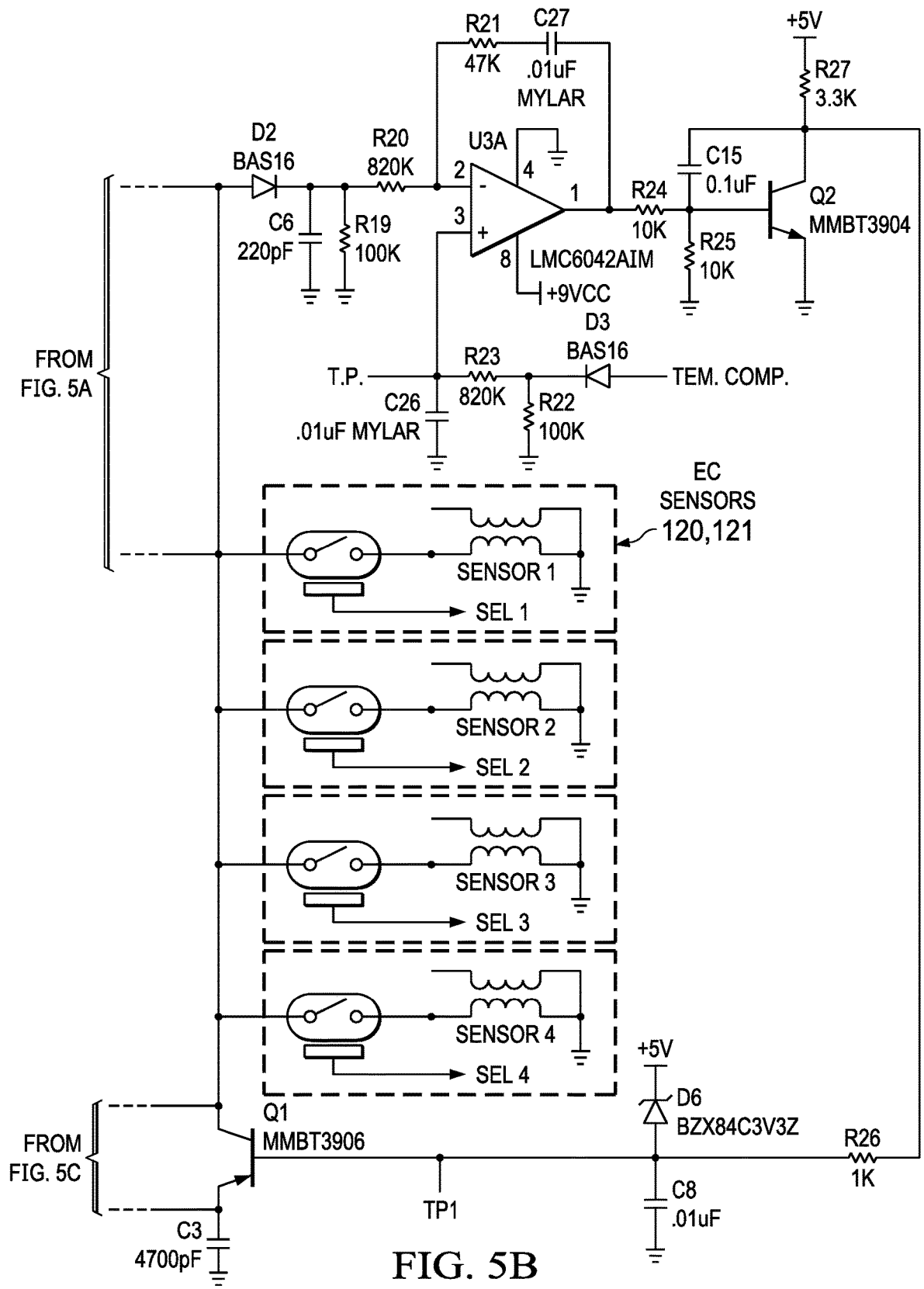
Figure 5C:
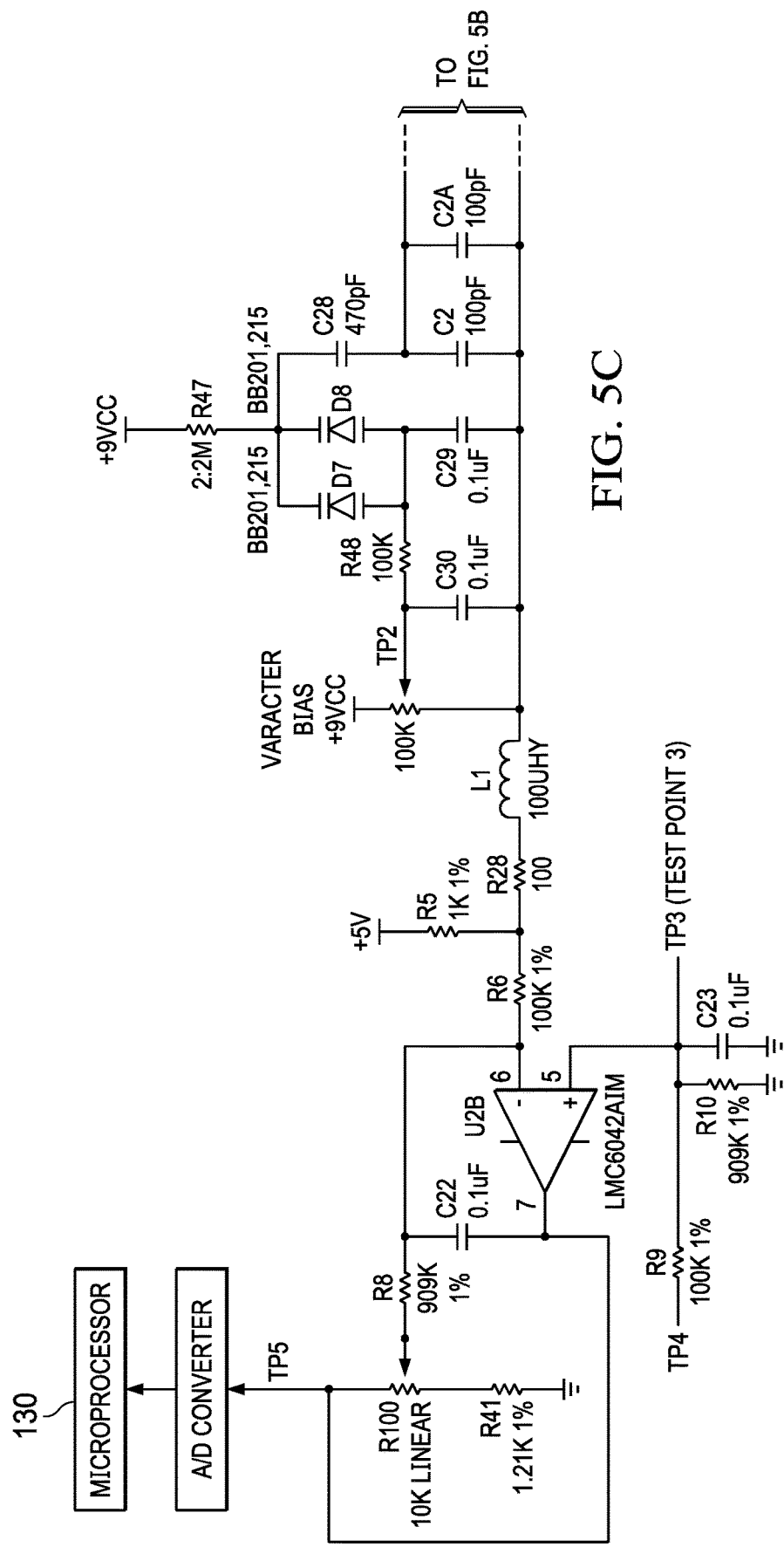

FIGS. 5A-5C exemplify an EC circuit board, wherein:

The output of a voltage regulator (+5 VDC) is provided to all circuit elements requiring a stable voltage.

The frequency (Fx) of a 4 Mhz. resonator, with built in loading capacitors, is used as the reference for one of the quadrature detector (U4) inputs. The derived oscillator frequency (Fo) of oscillator (Q1) serves as the other input to the quadrature detector. A lock condition happens when Fo and Fx are within a phase of 90 degrees of each other.

Once locked, the output of U3B, a positive DC voltage, serves as the AFC (Automatic Frequency Control) output voltage. This voltage is added to the RF voltage across the varactor tuning diodes D1 and D5 to maintain the "lock" from the cathode end. The reverse bias AFC voltage will cause the tuning diodes to change their capacitance inversely with this voltage, which will cause to raise or lower their capacitance, to keep the oscillators L C tank circuit tuned to Fx, much like a dc servo.

Tuning diodes D7 and D8 are used to initially set Fo of the L C tank circuit at the center of the AFC's locking range. This allows for automatic capture when the EC circuit is powered on.

The LC tank circuit inductance is composed of the inductance of the sensor transformers primary coil. The equivalent capacitance is the sum of: the capacitance of D7 and D8, +C2, +C2a, + the capacitance of D1 and D5, +C4.

The value of the inductance, for each of the EC sensors, is changed by the loading of the soils conductivity. This changes the resonant frequency of the loop. The phase lock loop ("PLL") is "tuned" by the varactors until the resonant frequency of the loop with the loaded inductor is the same as the frequency of the loop with unloaded inductors (in air).

Diode D2 is a high impedance peak detector of the L C tank circuit's RF voltage. The derived peak detector's output voltage is across load resister R19 and filter capacitor C6.

The derived peak detector output voltage, and the temperature compensation voltage which is applied to D3, are used to drive regulator amplifier U3A, which regulates the error difference between diodes D2 and D3, and results in a relatively constant output voltage over the operating range.

The regulator amplifier U3A drives current source Q2, which in turn drives oscillator Q1.

The initial voltage at the base of Q1 (in air) must be in the range of 3.80 to 3.83 VDC The output voltage of Q1 (Vpo) varies from close to zero, to a maximum peak voltage, linear with increasing base bias voltage, for any tank circuit load within the EC range. The tank circuit load is the load seen by the sensor transformers one turn secondary. Zener diode D6 is used to limit the base bias voltage of Q1, in case of a shorted sensor transformer secondary.

Any decrease in the load resistance of the sensor transformers secondary (sensing a lower EC) will cause the regulating amplifier U3A to hold Vpo constant, by increasing Vb of Q1, which will result in increasing its collector current.

Alignment/Calibration of the EC Board

With the EC sensor of interest in air:

Provide +9 VDC to pin 1, of U1, the +5 VDC voltage regulator.

The EC's micro will determine the temperature at the EC board, by comparing the voltage vs. temp for the on board temp sensor, against the actual measured voltage of the temp sensor.

Once the current temp at the board is determined, another look up table will provide the temp comp voltage which needs to be measured at pin 3, of U3A.

A voltage must be applied to the anode of D3, which is the combination of the temp comp voltage +0.6 volts, while monitoring pin 3, of U3A. This sets the temp comp voltage for the current board temp.

The initial voltage at the base of Q1 (in air) must be in the range of 3.80 to 3.83 VDC.

Monitor tp1, while varying the tuning voltage of diodes D7 and D8, using a starting voltage of 9 VDC (Vbat) at tp2, until the voltage at tp1 is 3.80 to 3.83 VDC.

Use look up table to set DPP1 to the "wiper" resistance value associated with 100% water.

Monitor tp3, while varying the voltage at tp4, until the voltage at tp3 (pin 5 of the balanced summing amplifier) is 4.00 volts.

Verify that the voltage at the cathode of D4 is 0.379 volts.

With the EC sensor of interest in low end standard EC solution (e.g., 300 uS):

Note: the standard EC values vs. the voltage at the cathode of D4 should preferably be at 20 uS increments (150 uS to 1800 uS).

Adjust the voltage at pin 5 of U2B until the voltage at the cathode of D4 measures the corresponding value from a look up table of the standard low end EC solution. The corresponding voltage at the cathode of D4 is scaled up until it is compatible with the input voltage of the microprocessor.

With the EC sensor of interest in a high end standard EC solution (1800 uS):

Use a high end standard EC solution value e.g., 1800 uS, measure voltage at cathode of D4, and compare to look up table of EC solutions vs. voltage at cathode of D4.

Establishing a Local EC Standard

Before installing the probe into the soil, local, initial calibration must be done, using local irrigation or tap water, with a known EC.

In air, R100, a digital potentiometer, is adjusted until the cathode of D4 reads 0.0.

With the lowest EC sensor in water of known EC, adjust R100, the digital pot, to the know salinity value.

This CAL value will be transferred to all the other EC sections.

Installed (in the Soil) Automatic Measurements

The micro will communicate with the capacitance to digital converter/temp sensor monitor chip, using a serial communication link, and the EC sensor measurement circuit.

The M/T/EC (moisture/temperature/EC) board will normally be dis-powered until the micro provides a battery voltage of +3.6 VDC to the dc to dc converter, which will provide +9 VDC and +5 VDC to the board's circuitry.

The micro will then enable temperature, and moisture measurements, and use these measurements to make temperature compensated EC measurement at level (n), where n=1 to 15.

The micro will provide a % moisture value for each level at which an EC measurement is to be made (in digital format).

The micro will apply a temp comp voltage for both the moisture, and EC measuring circuits, and will use the temperature measured at each level. The chip's internal temp sensor will automatically compensate for the chip's temperature changes.

The external temp sensor voltages will be used with a look up table to determine the temp comp voltage needed to be applied at pin 3, of U3A.

The micro will check that % moisture value is at least 85%, or EC measurement will not be made, and an error will be sent.

A look up table will be used to set DPP1 to the "wiper" resistance value associated with the % moisture value.

Voltages measured at the cathode of D4, this is the voltage equivalent of the soils EC at the level of the specified sensor.

The procedure will be repeated for each additional specified EC sensor, and using the % moisture at the sensor, provided by the capacitance to digital converter/temperature sensor monitor chip.

When the measurements are completed, the micro will indicate the end of measurements, and will dis-power the board.

There are a number of advantages associated with the invention. By way of example, but not limitation:

The probe can make direct measurements of absolute EC values, without the need to interpolate measured data.

The EC measurements reported are linear.

The EC measurements reported are linear for each sensor.

The EC measurements can be made in any soil type, or combinations of non-homogenous soils.

The EC measurements can be made at several soil depths, simultaneously, with each soil sensor being in a unique soil composition.

EC measurements can be made continually, or at fixed time intervals.

A wide range of EC measurement can be made, from 20 micro-Siemens, to 20,000 micro-Siemens.

The probes sensors, and circuit are temperature compensated for both the moisture, and EC functions.

Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered obvious and desirable by those skilled in the art based upon a review of the foregoing description of preferred embodiments. Accordingly, it is appropriate that the appended claims be construed broadly and in a manner consistent with the scope of the invention.

The invention claimed is:

1. A probe sensor for directly measuring electrical conductivity ("EC") of a medium, the probe sensor comprising:
   a tube having an outer wall and an inner wall, wherein the tube is fabricated from a non-metallic material;
   an EC board mounted on the tube;
   a microprocessor mounted on the EC board;

a plurality of radio frequency ("RF") transformers each comprising a primary and a secondary;

wherein each primary comprises a stainless steel sleeve positioned on the exterior of the outer wall of the tube for direct contact with the medium, wherein each sleeve defines two longitudinal slots on opposing sides of the tube, and wherein each sleeve is magnetically coupled to the secondary of the RF transformer;

wherein the secondary is positioned within the inner wall in alignment with slots of the sleeve, and is electrically coupled to the EC board;

wherein the secondary is configured to sense changes in a load by the primary;

a plurality of temperature sensors mounted on the tube and interposed between the inner wall and the outer wall of the tube, wherein one of the plurality of temperature sensors is positioned proximate to a corresponding one of the plurality of sleeves, wherein each temperature sensor is electrically coupled to the microprocessor; and a plurality of moisture sensors mounted on the tube and interposed between the inner wall and the outer wall of the tube, wherein one of the plurality of moisture sensors is positioned proximate to a corresponding one of the plurality of sleeves, wherein each moisture sensor is electrically coupled to the microprocessor.

2. The probe sensor of claim 1, further comprising a radio coupled to the microprocessor for receiving signals from the microprocessor and for transmitting the signals.

3. The probe sensor of claim 1, wherein the non-metallic material is polyvinyl chloride ("PVC").

4. The probe sensor of claim 1, wherein the EC board includes temperature compensated phase locked loop ("PLL") circuits to measure EC values of the medium.

5. The probe sensor of claim 1, wherein the medium is soil.

6. The probe sensor of claim 1, wherein the RF transformer is operative at a frequency of 4 Mhz.

7. The probe sensor of claim 1, wherein the non-metallic material is plastic.

* * * * *